United States Patent
Fair et al.

(10) Patent No.: US 12,345,786 B2
(45) Date of Patent: Jul. 1, 2025

(54) PROPELLER ECHO PLANAR TIME-RESOLVED IMAGING WITH DYNAMIC ENCODING

(71) Applicant: THE GENERAL HOSPITAL CORPORATION, Boston, MA (US)

(72) Inventors: Merlin John Casper Fair, Boston, MA (US); Kawin Setsompop, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 949 days.

(21) Appl. No.: 17/442,823

(22) PCT Filed: Mar. 26, 2020

(86) PCT No.: PCT/US2020/024964
§ 371 (c)(1),
(2) Date: Sep. 24, 2021

(87) PCT Pub. No.: WO2020/198475
PCT Pub. Date: Oct. 1, 2020

(65) Prior Publication Data
US 2022/0221540 A1    Jul. 14, 2022

Related U.S. Application Data

(60) Provisional application No. 62/824,583, filed on Mar. 27, 2019.

(51) Int. Cl.
*G01R 33/48*    (2006.01)
*A61B 5/055*    (2006.01)
(Continued)

(52) U.S. Cl.
CPC ......... *G01R 33/4824* (2013.01); *A61B 5/055* (2013.01); *G01R 33/5608* (2013.01); *G01R 33/56509* (2013.01); *A61B 2560/0223* (2013.01)

(58) Field of Classification Search
CPC ............ G01R 33/4824; G01R 33/5608; G01R 33/56509; A61B 5/055; A61B 2560/0223
See application file for complete search history.

(56) References Cited

U.S. PATENT DOCUMENTS

| | | | | |
|---|---|---|---|---|
| 2008/0303521 A1* | 12/2008 | Beatty | ............... | G01R 33/5611 324/307 |
| 2014/0003694 A1* | 1/2014 | Weng | ............... | G01R 33/56509 382/131 |

(Continued)

FOREIGN PATENT DOCUMENTS

WO    2019036833 A1    2/2019

OTHER PUBLICATIONS

Reeder, S., et al., "Referenceless Interleaved Echo-Planar Imaging," Magnetic Resonance Medicine. vol. 41(1), 1999. p. 87-94 (Year: 1999).*

(Continued)

*Primary Examiner* — Sean A Frith
(74) *Attorney, Agent, or Firm* — QUARLES & BRADY LLP

(57) ABSTRACT

Magnetic resonance imaging ("MRI") using a PROPELLER echo-planar time-resolved imaging with dynamic encoding ("PEPTIDE") scheme is described. The PEPTIDE scheme combines a PROPELLER-style trajectory with an echo-planar time-resolved imaging ("EPTI") acquisition framework, along with dynamic-updating of sensitivity-encoding information.

18 Claims, 5 Drawing Sheets

(51) Int. Cl.
*G01R 33/56* (2006.01)
*G01R 33/565* (2006.01)

(56) References Cited

U.S. PATENT DOCUMENTS

| | | | |
|---|---|---|---|
| 2014/0111203 A1* | 4/2014 | Zhou | G01R 33/56518 |
| | | | 324/309 |
| 2014/0225612 A1 | 8/2014 | Polimeni et al. | |
| 2014/0375318 A1* | 12/2014 | Dagher | G01R 33/243 |
| | | | 324/309 |
| 2016/0061924 A1* | 3/2016 | Pipe | G01R 33/56509 |
| | | | 382/131 |
| 2016/0139224 A1* | 5/2016 | Assif | A61B 8/4416 |
| | | | 600/411 |
| 2018/0188343 A1* | 7/2018 | Liu | A61B 5/055 |
| 2019/0064292 A1* | 2/2019 | Leghissa | G01R 33/5608 |
| 2019/0139274 A1* | 5/2019 | Park | G01R 33/5611 |
| 2019/0369185 A1 | 12/2019 | Setsompop et al. | |
| 2019/0369186 A1 | 12/2019 | Setsompop et al. | |

OTHER PUBLICATIONS

Bruder, H., et al., "Image Reconstruction for Echo Planar Imaging with Nonequidistant k-Space Sampling," Magnetic Resonance in Medicine. vol. 23, 1992. p. 311-323 (Year: 1992).*
PCT/US2020/024964—International Search Report and Written Opinion—Jun. 26, 2020.
Breuer, et al., "Zigzag Sampling for Improved Parallel Imaging". 2008. Magnetic Resonance in Medicine 60:474-478.

* cited by examiner

FIG. 1A EPTI Sampling

FIG. 1B Conventional EPTI

FIG. 1C PEPTIDE

PROPELLER ECHO PLANAR TIME-RESOLVED IMAGING WITH DYNAMIC ENCODING

CROSS-REFERENCE TO RELATED APPLICATIONS

This application is a U.S. National Stage of International Application No. PCT/US2020/024964 filed Mar. 26, 2020 which claims the benefit of U.S. Provisional Patent Application Ser. No. 62/824,583, filed on Mar. 27, 2019, and entitled "PROPELLER ECHO PLANAR TIME-RESOLVED IMAGING WITH DYNAMICE ENCODING (PEPTIDE)," which is herein incorporated by reference in its entirety.

STATEMENT REGARDING FEDERALLY SPONSORED RESEARCH

This invention was made with government support under MH116173, EB020613, EB019437, EB025162, EB015896, RR023401, RR019307, RR019254, and RR023043 awarded by the National Institutes of Health. The government has certain rights in the invention.

BACKGROUND

Echo-planar imaging ("EPI") is a well-established technique for rapid magnetic resonance imaging ("MRI") acquisition, with either single-shot or multi-shot varieties used in a wide range of applications, including diffusion, perfusion, and functional MRI. Despite the fast acquisition enabled by EPI, the extended readout duration comes with well-known drawbacks: B0 inhomogeneity induced phase accrual along the phase-encoding direction, leading to geometric distortions of the image and T2/T2* decay during the readout, resulting in spatial filtering (blurring). Additionally, while EPI allows rapid image acquisition, the extended readout duration places a limit on the timing between TEs, restricting its application to multi-echo techniques.

Echo-planar time-resolved imaging ("EPTI") is a recently developed multi-shot EPI-based technique that can rapidly create a large time-series of multi-contrast T2 and T2*-weighted images, free from image distortion and blurring. This can enable production of accurate T2, T2*, proton-density, and QSM maps, all with whole-brain coverage from a single acquisition of less than one minute.

EPTI creates time-resolved datasets, with complete k-t coverage across the EPI readout window at a time-resolution of an echo spacing (e.g., about 1 ms). This allows images to be produced for each time point along the EPI readout, free from associated distortion and blurring caused by $B_0$-inhomogeneity induced phase and T2*decay. EPTI acquires k-t space through a $k_y$-segmented traversal, using a highly-undersampled zig-zag trajectory, where the even and odd diagonal transversals of this trajectory sample complementary neighboring $k_y$-points. Such spatiotemporal CAIPI-sampling facilities accurate reconstruction of highly undersampled $k_y$-t space through $B_0$-inhomogeneity-informed parallel imaging. With this time-resolved approach, the EPI readout in a dual gradient- and spin-echo EPTI sequence has been used to efficiently acquire large time-series of T2 and T2*-weighted images. The $k_y$-segmented acquisition facilitates very rapid acquisitions, however, this also leads to a potential sensitivity to inter-segment shot-to-shot motion and $B_0$ phase variations.

Radial and pseudo-radial trajectories are known for their inherent motion robust properties. Continual resampling of central k-space ensures tolerance to inter-shot motion, as well as enabling further motion- and phase-correction methods. In addition, such trajectories cope well with sub-Nyquist sampling and combine well with many advanced reconstruction techniques.

SUMMARY OF THE DISCLOSURE

The present disclosure addresses the aforementioned drawbacks by providing a method for producing an image with a magnetic resonance imaging ("MRI") system by acquiring data with the MRI system by sampling a hybrid space along a zig-zag trajectory within each of a plurality of k-space blades, where the hybrid space comprises a first axis along a temporal dimension and a second axis along a phase-encoding k-space dimension. An image is then reconstructed from the acquired data.

It is another aspect of the present disclosure to provide a method for producing an image with an MRI system, in which data are acquired with the MRI system by sampling k-space in a plurality of k-space blades, where k-space is sampled within each k-space blade along a plurality of interleaved phase encoding lines such that temporally adjacent phase encoding lines are separated in time by a first temporal spacing and phase encoding lines that are adjacent in k-space are separated in time by a second temporal spacing that is greater than the first temporal spacing. An image is then reconstructed from the acquired data by reconstructing a blade image for each k-space blade and combining the blade images, generating output as the reconstructed image.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for magnetic resonance imaging ("MRI") using a PROPELLER echo-planar time-resolved imaging with dynamic encoding ("PEPTIDE") scheme. The PEPTIDE scheme combines a PROPELLER-style trajectory with an echo-planar time-resolved imaging ("EPTI") acquisition framework, along with dynamic-updating of sensitivity-encoding information. Based in part on this modification, the PEPTIDE acquisition provides an improved robustness to motion and phase-variations, and also utilizes benefits conferred from radial type acquisitions, such as resilience to undersampling. Given this robustness to motion, the PEPTIDE acquisition provides specific advantages for rapidly acquiring data from adult subjects, as well as patient populations that are traditionally difficult to scan due to motion and/or patient discomfort, such as pediatric patient populations or geriatric patient populations.

Advantageously, the PEPTIDE acquisition scheme described in the present disclosure enables the creation of a large multi-contrast time-series of distortion-free images in a short acquisition time, with improved tolerance to the presence of motion. For example, the PEPTIDE sequence can be implemented in any situation that calls for highly motion-robust rapid acquisition of different contrasts. This includes T2, T2* and T1 (if combined with inversion preparation) mapping, quantitative susceptibility mapping ("QSM"), susceptibility-weighted imaging ("SWI"), perfusion imaging, diffusion imaging, and functional MRI ("fMRI"). From these results, synthetic contrasts can also be generated.

EPTI is a multi-shot EPI-based technique that can rapidly create a large time-series of multi-contrast T2-weighted and T2*-weighted images in which image distortion and blurring are significantly mitigated. EPTI uses a highly efficient sampling strategy, which is performed through EPI readouts that are segmented along the phase encoding direction, but extended through time. This creates an undersampled hybrid space spanned by the phase encoding dimension and the temporal dimension, which as one example may be spanned by the $k_y$ dimension in k-space and the temporal dimension, t, and thus may be referred to as $k_y$-t space. In this hybrid space, neighboring $k_y$ points are closely separated in time, such that with appropriate reconstruction the formation of a time-series of images with differing contrasts can be generated at a temporal resolution equal to the echo-spacing.

The images of this time-series are therefore free of the typical $B_0$-inhomogeneity and T2* decay limitations of EPI imaging. The resulting image series enables many mapping techniques from just a single rapid acquisition. However, the sampling scheme used in EPTI necessitates the combination of the acquired segments prior to reconstruction. In doing so, there is increased sensitivity to shot-to-shot motion and $B_0$ phase variations.

Figure 1:
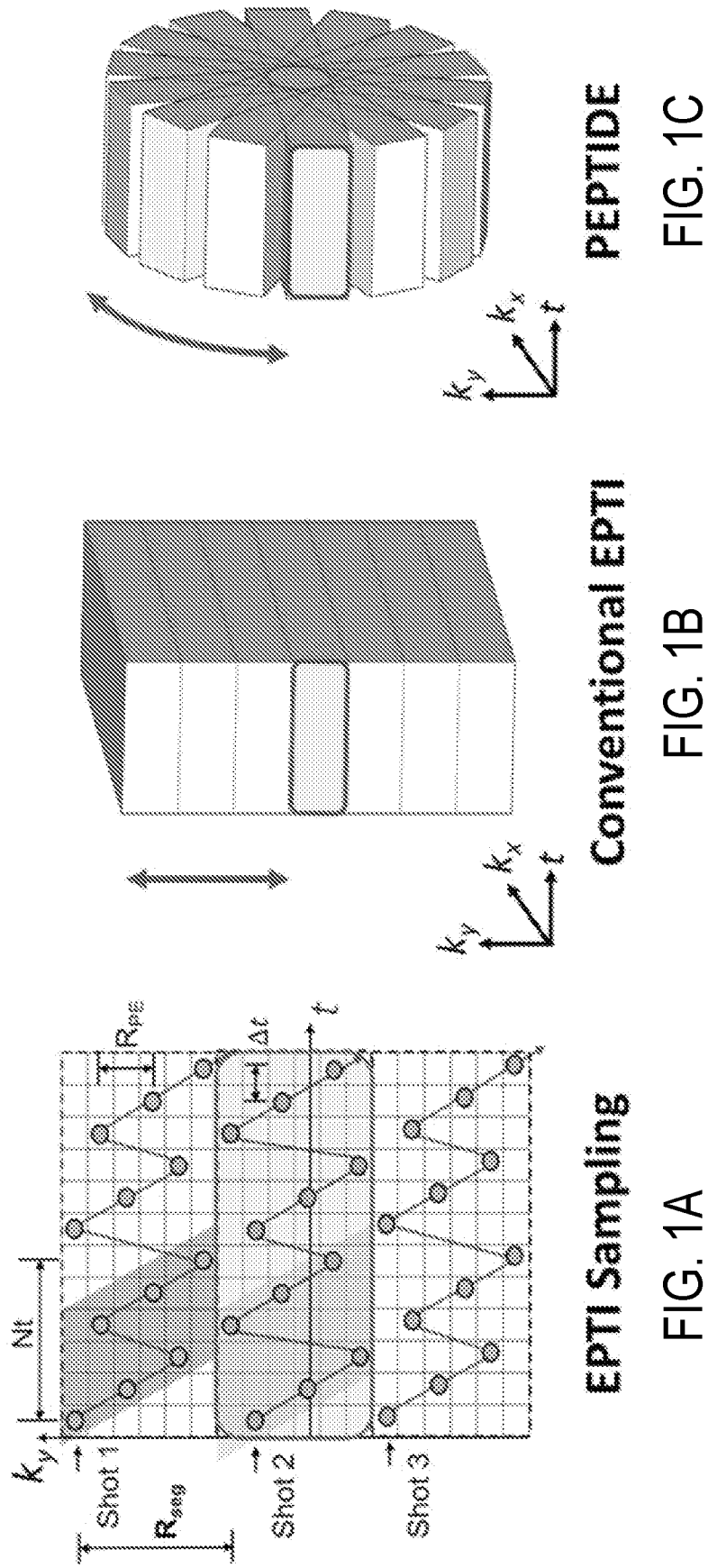
FIGS. 1A-1C show examples of an echo-planar time-resolve imaging ("EPTI") sampling pattern (FIG. 1A), a conventional EPTI acquisition scheme (FIG. 1B) and a PROPELLER echo-planar time-resolved imaging with dynamic encoding ("PEPTIDE") acquisition scheme.

In general, an EPTI approach acquires k-t space through a multi-shot $k_y$-segmented traversal using a highly undersampled zig-zag trajectory across each segment, as shown in FIGS. 1A and 1B. The temporal dimension represents the echo time ("TE") of each phase-encode line during the echo-train readout. If $k_y$-t space is fully sampled, a complete image with consistent phase accumulation and signal decay can be generated for each TE point from the corresponding $k_x$-$k_y$ data. This gives a large time-series of contrast-varying, distortion-free images, with a temporal spacing ($\Delta t$) equal to that of the EPI echo spacing.

The segmented zig-zag traversal ensures that the phase changes between neighboring acquired k-space points are minimized, while the jittered diagonal transversals of odd and even numbered $k_y$ points mean that complementary neighboring $k_y$ points are sampled in a spatiotemporal controlled aliasing in parallel imaging ("CAIPI") sampling pattern. This enables accurate reconstruction of the highly undersampled $k_y$-t space through $B_0$ inhomogeneity-informed parallel imaging, which uses GRAPPA-like compact kernels that utilize the small and spatially smooth phase differences between the neighboring data points in $k_y$-t space.

Figure 2:
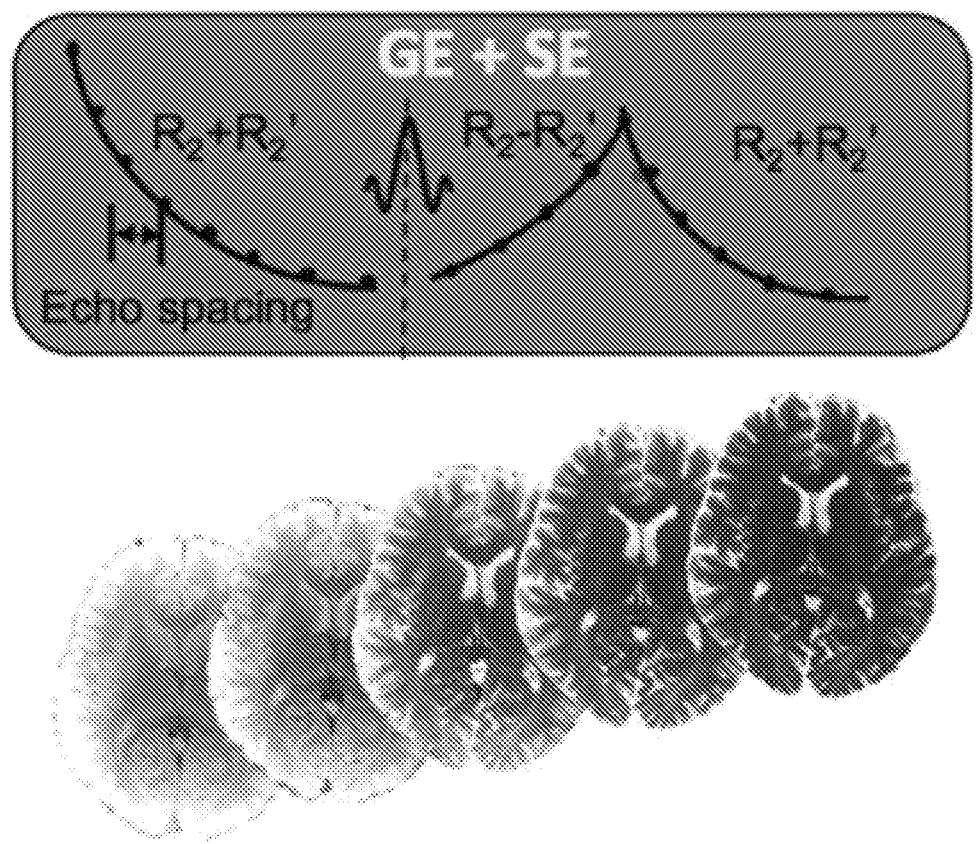
FIG. 2 depicts graphic illustrations of example signal evolution curves for a gradient-echo and spin-echo pulse sequence, and a corresponding multi-contrast image series.

As an example, in typical brain imaging situations, approximately 25-40 $k_y$ encoding lines ($R_{SEG}$) can be covered with each EPTI shot when a $k_y$ sampling distance ($R_{PE}$) of 4× Nyquist is used (FIG. 1A). This results in a 7-9 EPTI-shot acquisition for 1-mm in-plane resolution imaging. This approach can be, for example, applied to the EPI readout in a gradient-echo sequence, as well as for a dual gradient echo-spin echo ("GESE") EPTI sequence. The choice of sequence affects the signal curves that are sampled in $k_y$-t space, as shown in FIG. 2, and thus the quantitative maps that can be derived from the acquisition (e.g., the time series of differing image contrasts shown in FIG. 2).

As noted above, the PEPTIDE acquisition scheme described in the present disclosure extends the EPTI technique through the introduction of a PROPELLER style component to the acquisition. For example, the segments of varying $k_y$-positions that are used in EPTI are instead repeatedly acquired as central segments, but with varying rotations in the $k_y$-$k_x$ plane, as shown in FIG. 1C. These rotations in the acquisition allow the collection of k-space to be built up in a pseudo-radial manner. Additionally, these PEPTIDE segments additionally extend the acquisition through time. As such, the reconstruction of complete "k-t" space is still possible with the PEPTIDE acquisition. The rotational element of the acquisition provides a far greater robustness to motion due to the continual sampling of the k-space center with every segment, and allows further correction to the data on a blade-by-blade basis. In addition, such an acquisition allows for potential incorporation of advanced reconstruction techniques that utilize a diffuse undersampling pattern for even further acceleration.

Thus, the PEPTIDE approach samples k-t space with a zig-zag segmental pattern, similar to EPTI. However, instead of sampling different segments with shifts along $k_y$, PEPTIDE repeatedly acquires central segments but with varying rotations in the $k_y$-$k_x$ plane, as mentioned above and shown in FIG. 1C. As compared with EPTI, this is achieved in the sequence through replacement of the shot-to-shot $k_y$ shifts with shot-dependent rotation in the $k_y$-$k_x$ plane.

Consistent with previous EPTI definitions, $R_{PE}$ is defined as the spacing between sequential phase-encode acquisitions, with each diagonal line of acquisitions covering a total distance in the phase-encode direction that is defined as $R_{SEG}$. For EPTI, the number of segments ($N_{seg}$) required for complete k-space coverage ($-k_{y,max}$ to $+k_{y,max}$) is dependent on the value of $R_{SEG}$.

Similarly, for PEPTIDE, the number of acquired blades ($N_b$) required to achieve full k-space sampling is also dependent on $R_{SEG}$ and is related to the EPTI $N_{seg}$ equivalent through $$N_{b,full} = \left(\frac{\pi}{2}\right) \times N_{seg,full}$$

to account for the radial coverage. Although more shots are used to provide full Nyquist coverage in PEPTIDE, this comes with the benefit of motion robustness. Additionally, the radial sampling with an oversampled k-space center provided by PEPTIDE provides the ability to still achieve reasonable reconstruction in the presence of certain levels of angular undersampling.

In some embodiments, simultaneous multislice ("SMS") acquisitions can be implemented in the PEPTIDE methods described in the present disclosure. As an example, different data samples in an EPTI sampling trajectory within a given k-space blade can be with two different $k_z$ encodings, $k_{z,1}$ and $k_{z,2}$, to encode and acquire the two slices at the same time.

When implementing the PEPTIDE methods described in the present disclosure to time-series acquisitions (e.g., in fMRI, perfusion imaging, diffusion imaging), random undersampling, or some appropriate reordering, of PEPTIDE blades across TRs in conjunction with a spatiotemporal constrained reconstruction can be used. In doing so, higher temporal sampling with PEPTIDE can be achieved. As one non-limiting example, instead of creating an image only after 10 TRs in order to fully sample $k_x$-$k_y$, using a random PEPTIDE-blade acquisitions across TRs together with a constrained reconstruction can enable an image to be produced every third TR.

Figure 3:
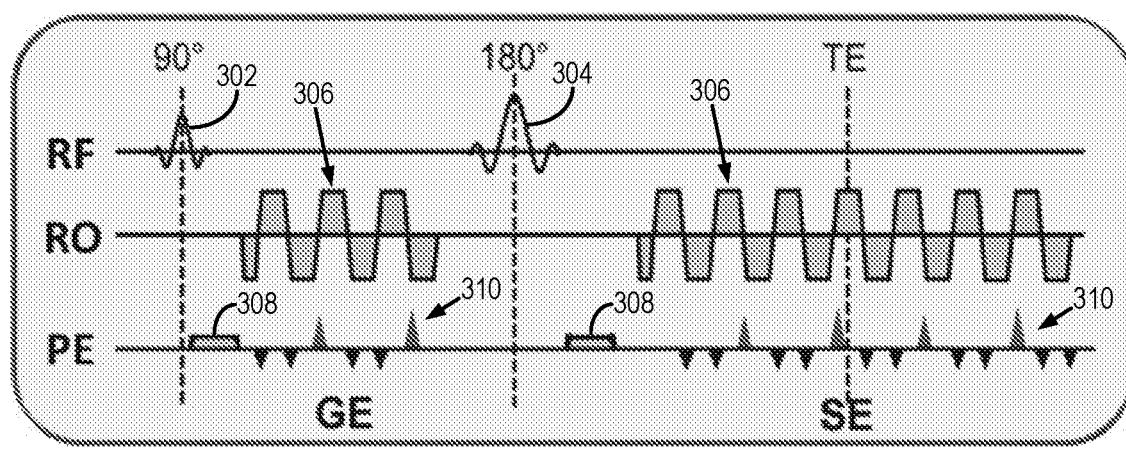
FIG. 3 is an example of a gradient-echo and spin-echo ("GESE") PEPTIDE pulse sequence for one shot, which can be implemented with some embodiments described in the present disclosure.

An example of a GESE pulse sequence that can be used to implement a PEPTIDE acquisition is shown in FIG. 3. The pulse sequence includes a radio frequency ("RF") excitation pulse 302 that is played out to produce transverse magnetization (e.g., in one or more prescribed imaging slices). A refocusing RF pulse 304 is later applied to refocus transverse spin magnetization in the one or more prescribed slice locations. Frequency encoding gradients 306 are applied in both a gradient echo ("GE") readout occurring before the application of the refocusing RF pulse 304 and a spin echo ("SE") readout occurring after the refocusing RF pulse 304. The target EPTI sampling pattern in each k-space blade is achieved by phase encoding gradients 308 and the series of phase encoding gradient blips 310. Additional gradients can then be used in each repetition in order to rotate the EPTI sampling pattern in the $k_y$-$k_x$ plane, as described above.

Figure 4:
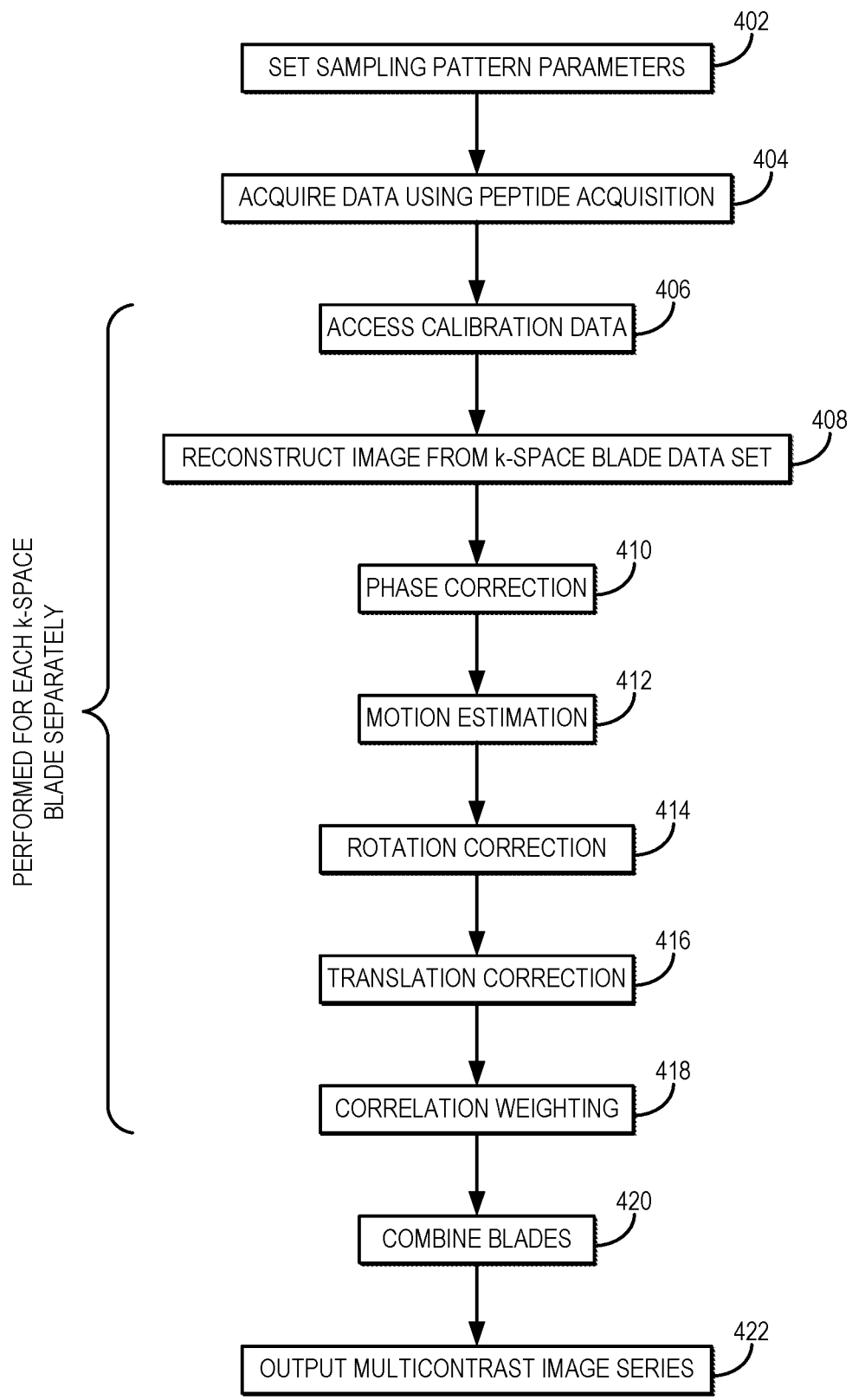
FIG. 4 is a flowchart setting forth the steps of an example method for generating images with an MRI system using a PEPTIDE acquisition scheme and corresponding image reconstruction framework.

Referring now to FIG. 4, a flowchart is illustrated as setting forth the steps of an example method for acquiring data using a PEPTIDE acquisition and reconstructing one or more images from the acquired data.

The method includes setting parameters of the sampling pattern to be used for acquiring data, as indicated at step 402. The parameters can be selected via user input to a computer system that then communicates those parameters to the MRI system. For instance, the parameters can be entered via a user interface, which may be a graphical user interface. As described above, the parameters can include a first temporal spacing, $\Delta t$, between temporally adjacent data samples in each section of the hybrid space sampling pattern, a phase encoding spacing, $R_{PE}$, between temporally adjacent data samples in each section of the hybrid space sampling pattern, a second temporal spacing, $N_t$, between temporally adjacent sections of the hybrid space sampling pattern, the number of sections in the hybrid space sampling pattern, the number of shots/segments of the phase encoding dimension, the number of k-space blades, and so on.

After the parameters for the hybrid space sampling pattern have been selected they are communicated to the MRI system, which is then operated to perform a PEPTIDE pulse sequence to acquire data according to the defined hybrid space sampling pattern, as indicated at step 404. As described above, data can be acquired in one or more shots. The acquired data undersample the hybrid space in order to accelerate the data acquisition process; however, using the hybrid space sampling patterns described in the present disclosure $B_0$-inhomogeneity induced phase errors and $T_2^*$ decay related blurring are reduced. Further, as described above, the PEPTIDE pulse sequence is robust against patient motion, such that motion-induced errors are reduced in the acquired data.

Reconstructing images from data acquired using a PEPTIDE pulse sequence includes accessing calibration data with a computer system, as indicated at step 406. Accessing these data can include retrieving the data from a memory or other suitable data storage device or medium. Alternatively, accessing these data can include acquiring the data with an MRI system and transferring or otherwise communicating the data to the computer system, which may be a part of the MRI system.

As one example, the calibration data can be acquired using a low-resolution calibration scan. For instance, a short calibration scan of a small, fully sampled $k_y$-t region can be implemented, and these calibration data can be used to train reconstruction kernels. As described below, separate calibration data do not need to be acquired for each blade. Rather, an identical single calibration scan can be used for all blades by applying a rotation to the calibration data before calculation of the reconstruction kernels for each blade. This avoids the necessity to collect additional reference data for each blade.

As also described below, for any reconstructed blade in which significant motion is detected, the estimated motion can be used to update the rotation that needs to be applied to the calibration data for the reconstruction kernel calculation of that blade. The reconstruction kernel for that blade can then recalculated and the reconstruction performed again with the updated reconstruction kernel in order to achieve improved results. In doing so, it is possible to dynamically update the parallel imaging reconstruction to ensure maximal accuracy across all blades and at all of the time points.

Referring still to FIG. 4, the calibration data are then adjusted to match the current k-space blade being reconstructed, as described above and indicated at step 408. For example, a rotation can be applied to the calibration data such that the calibration data are rotated to match the angular orientation of the k-space blade being reconstructed.

Each k-space blade is then separated reconstructed, as indicated at step 410. As one example, a parallel imaging reconstruction, such as a $B_0$-informed parallel imaging reconstruction, can be implemented. As a non-limiting example, a PE-t GRAPPA reconstruction can be implemented to reconstruct each k-space blade. This is equivalent to reconstruction of only the central segment of an EPTI data set, which yields a time-series data set with low resolution in one spatial dimension. As another example, a tilted-CAIPI reconstruction such as those described in co-pending U.S. Patent Appln. Pub. No. US 2019/0369186, which is herein incorporated by reference in its entirety.

A PROPELLER-style reconstruction/combination across the blades and time series, implementing various motion-correction techniques for inter-blade motion/phase prior to combination through a gridding method, can then be performed, as follows.

First, a phase correction is initially applied to each blade, as indicated at step 412. As one example, the phase correction can be implemented by subtracting a triangularly windowed phase of each blade from itself in order to remove low-frequency spatially varying components. This corrects for any offset in the center of the blade rotation, and removes $B_0$ variation phase.

An affine (e.g., three degrees-of-freedom) transformation is calculated between the blade data and a common reference, for each blade, to estimate the rotational and translational motion that has occurred, as indicated at step 414. As one example, the motion estimation can use the centrally overlapping region of each blade to analyze both the real-component k-space correlations at various rotations as well as the peak of the complex data convolution, both against a fixed reference.

Motion correction can then be performed either for every time point within each PEPTIDE blade acquisition or for a temporal average per blade if the temporal footprint of each blade acquisition is deemed short enough (e.g., less than 150 ms). For instance, an adjustment is made to the $k_x$-$k_y$ trajectory for each blade to correct for the estimated rotational motion, as indicated at step 416. If the rotation correction applied is above a selected threshold, then the corresponding calibration data can also be corrected and steps 410-416 repeated for the given k-space blade until the rotation correction is below the desired threshold. The appropriate phase adjustment (e.g., linear phase slope) can also applied to each blade k-space data set to correct for the translational motion, as indicated at step 418.

The translation and rotation corrected blades are then cross-correlated, so that a reduced weighting can be appropriately applied to blades that are poorly correlated, to alleviate the artifacts due to through-plane or non-rigid motion, as indicated at step 420. The reconstructed and corrected blades can then be combined, as indicated at step 422. For example, the blades can be combined through a gridded process across all time points, generating output as the multi-contrast image time series after Fourier transform, as indicated at step 424. As one non-limiting example, gridding can be performed with an oversampling factor of two and a Kaiser-Bessel kernel width of five, with the application of an iteratively calculated density compensation function. Blade weighting was applied to the density compensation function with weighting coefficients calculated from the cross-correlation process.

The reconstructed multi-contrast images can be displayed to a user, or stored for later use or processing. For example, quantitative parameter maps can be generated from the multi-contrast images, such as T1 maps, T2 maps, T2* maps, diffusion coefficient maps, perfusion parameter maps, quantitative susceptibility maps, and so on.

Figure 5:
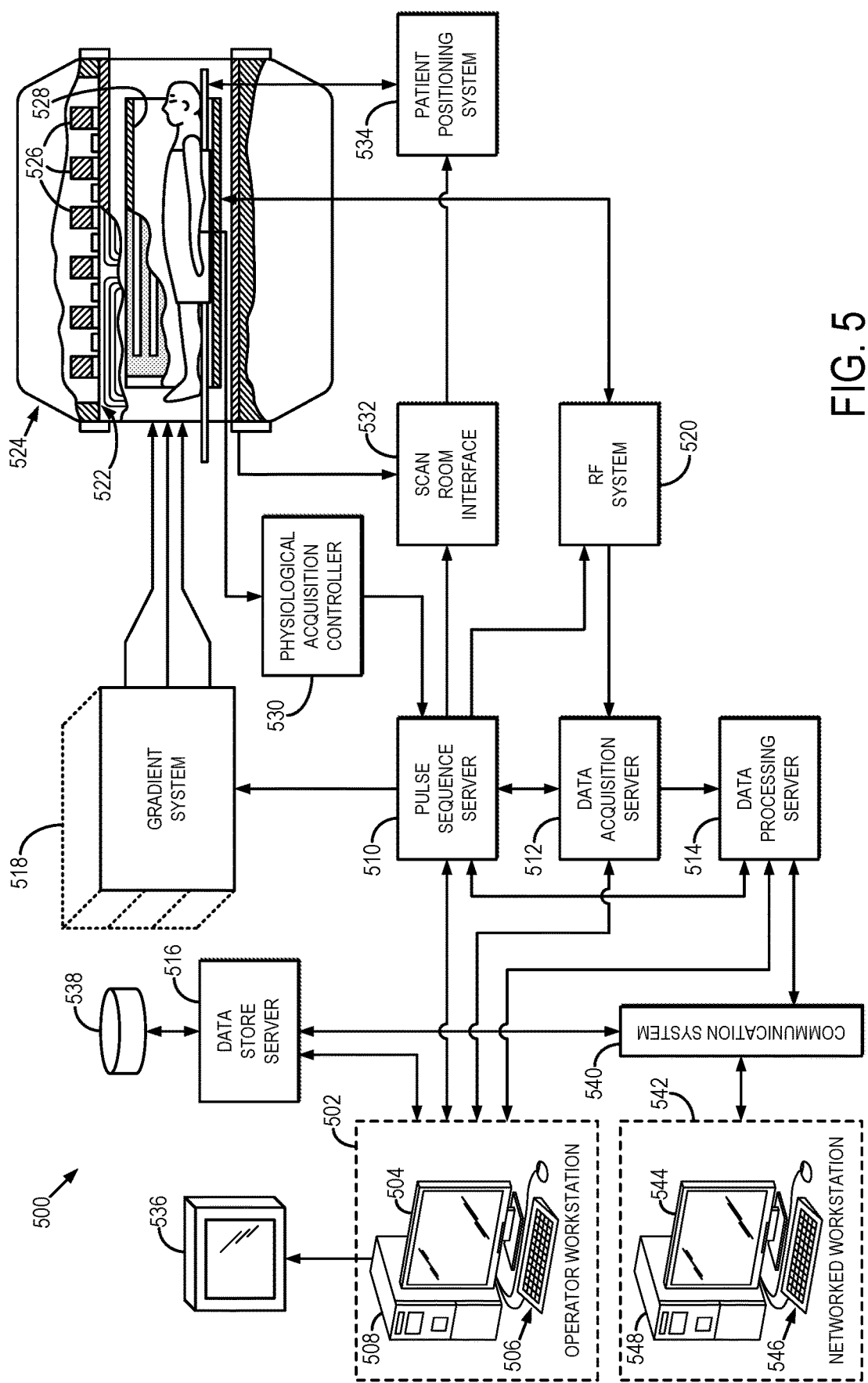
FIG. 5 is a block diagram of an example MRI system that can implement the methods described in the present disclosure.

Referring particularly now to FIG. 5, an example of an MRI system 500 that can implement the methods described here is illustrated. The MRI system 500 includes an operator workstation 502 that may include a display 504, one or more input devices 506 (e.g., a keyboard, a mouse), and a processor 508. The processor 508 may include a commercially available programmable machine running a commercially available operating system. The operator workstation 502 provides an operator interface that facilitates entering scan parameters into the MRI system 500. The operator workstation 502 may be coupled to different servers, including, for example, a pulse sequence server 510, a data acquisition server 512, a data processing server 514, and a data store server 516. The operator workstation 502 and the servers 510, 512, 514, and 516 may be connected via a communication system 540, which may include wired or wireless network connections.

The pulse sequence server 510 functions in response to instructions provided by the operator workstation 502 to operate a gradient system 518 and a radiofrequency ("RF") system 520. Gradient waveforms for performing a prescribed scan are produced and applied to the gradient system 518, which then excites gradient coils in an assembly 522 to produce the magnetic field gradients $G_x$, $G_y$, and $G_z$ that are used for spatially encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil to perform the prescribed magnetic resonance pulse sequence. Responsive magnetic resonance signals detected by the RF coil 528, or a separate local coil, are received by the RF system 520. The responsive magnetic resonance signals may be amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the prescribed scan and direction from the pulse sequence server 510 to produce RF pulses of the desired frequency, phase, and pulse amplitude waveform. The generated RF pulses may be applied to the whole-body RF coil 528 or to one or more local coils or coil arrays.

The RF system 520 also includes one or more RF receiver channels. An RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 510 may receive patient data from a physiological acquisition controller 530. By way of example, the physiological acquisition controller 530 may receive signals from a number of different sensors connected to the patient, including electrocardiograph ("ECG") signals from electrodes, or respiratory signals from a respiratory bellows or other respiratory monitoring devices. These signals may be used by the pulse sequence server 510 to synchronize, or "gate," the performance of the scan with the subject's heart beat or respiration.

The pulse sequence server 510 may also connect to a scan room interface circuit 532 that receives signals from various sensors associated with the condition of the patient and the magnet system. Through the scan room interface circuit 532, a patient positioning system 534 can receive commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, so that data is not lost by data overrun. In some scans, the data acquisition server 512 passes the acquired magnetic resonance data to the data processor server 514. In scans that require information derived from acquired magnetic resonance data to control the further performance of the scan, the data acquisition server 512 may be programmed to produce such information and convey it to the pulse sequence server 510. For example, during pre-scans, magnetic resonance data may be acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also process magnetic resonance signals used to detect the arrival of a contrast agent in a magnetic resonance angiography ("MRA") scan. For example, the data acquisition server 512 may acquire magnetic resonance data and processes it in real-time to produce information that is used to control the scan.

The data processing server 514 receives magnetic resonance data from the data acquisition server 512 and processes the magnetic resonance data in accordance with instructions provided by the operator workstation 502. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 514 are conveyed back to the operator workstation 502 for storage. Real-time images may be stored in a data base memory cache, from which they may be output to operator display 502 or a display 536. Batch mode images or selected real time images may be stored in a host database on disc storage 538. When such images have been reconstructed and transferred to storage, the data processing server 514 may notify the data store server 516 on the operator workstation 502. The operator workstation 502 may be used by an operator to archive the images, produce films, or send the images via a network to other facilities.

The MRI system 500 may also include one or more networked workstations 542. For example, a networked workstation 542 may include a display 544, one or more input devices 546 (e.g., a keyboard, a mouse), and a processor 548. The networked workstation 542 may be located within the same facility as the operator workstation 502, or in a different facility, such as a different healthcare institution or clinic.

The networked workstation 542 may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542.

Figure 6:
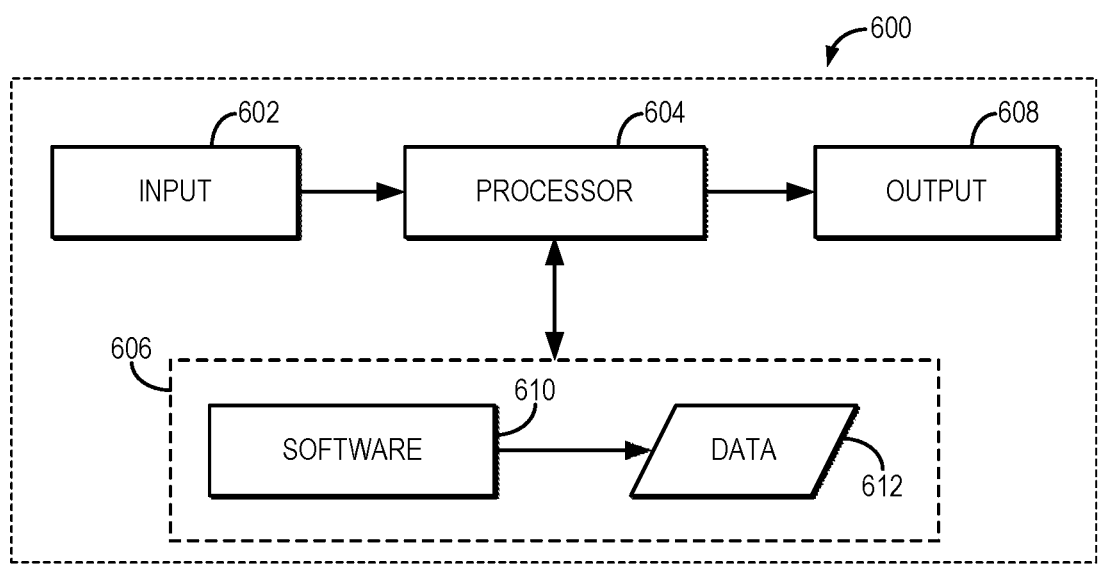
FIG. 6 is a block diagram of an example computer system that can implement methods described in the present disclosure, such as methods for reconstructing images from data acquired with a PEPTIDE acquisition.

Referring now to FIG. 6, a block diagram of an example of a computer system 600 that can perform the methods described in the present disclosure is shown. The computer system 600 generally includes an input 602, at least one hardware processor 604, a memory 606, and an output 608. Thus, the computer system 600 is generally implemented with a hardware processor 604 and a memory 606.

In some embodiments, the computer system 600 can be a workstation, a notebook computer, a tablet device, a mobile device, a multimedia device, a network server, a mainframe, one or more controllers, one or more microcontrollers, or any other general-purpose or application-specific computing device.

The computer system 600 may operate autonomously or semi-autonomously, or may read executable software instructions from the memory 606 or a computer-readable medium (e.g., a hard drive, a CD-ROM, flash memory), or may receive instructions via the input 602 from a user, or any another source logically connected to a computer or device, such as another networked computer or server. Thus, in some embodiments, the computer system 600 can also include any suitable device for reading computer-readable storage media.

In general, the computer system 600 is programmed or otherwise configured to implement the methods and algorithms described in the present disclosure. For instance, the computer system 600 can be programmed to reconstruct images from data acquired using a PEPTIDE pulse sequence using a suitable reconstruction algorithm, such as those described in the present disclosure.

The input 602 may take any suitable shape or form, as desired, for operation of the computer system 600, including the ability for selecting, entering, or otherwise specifying parameters consistent with performing tasks, processing data, or operating the computer system 600. In some aspects, the input 602 may be configured to receive data, such as data acquired with an MRI system. Such data may be processed as described above to reconstruct images. In addition, the input 602 may also be configured to receive any other data or information considered useful for reconstructing images using the methods described above.

Among the processing tasks for operating the computer system 600, the one or more hardware processors 604 may also be configured to carry out any number of post-processing steps on data received by way of the input 602. For instance, one or more parameter maps can be generated from multi-contrast images reconstructed from data acquired with a PEPTIDE pulse sequence.

The memory 606 may contain software 610 and data 612, such as data acquired with an MRI system, and may be configured for storage and retrieval of processed information, instructions, and data to be processed by the one or more hardware processors 604. In some aspects, the software 610 may contain instructions directed to reconstructing images from data acquired with a PEPTIDE pulse sequence using a suitable reconstruction algorithm.

In addition, the output 608 may take any shape or form, as desired, and may be configured for displaying reconstructed images, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for producing an image with a magnetic resonance imaging (MRI) system, the steps comprising:
   a) acquiring data with an MRI system by sampling a hybrid space along a zig-zag trajectory within each of a plurality of k-space blades, wherein the hybrid space comprises a first axis along a temporal dimension and a second axis along a phase-encoding k-space dimension, and
   b) reconstructing an image from the acquired data.

2. The method of claim 1, wherein reconstructing an image from the acquired data comprises:
   reconstructing a plurality of blade images, each blade image being reconstructed from the hybrid space data acquired for a given k-space blade; and
   combining the plurality of blade images, generating output as the reconstructed image.

3. The method of claim 2, wherein reconstructing each blade image comprises:
   reconstructing the blade image from the hybrid space data acquired for the given k-space blade;
   applying a phase correction to the blade image;
   estimating motion parameters based on the hybrid space data in the given k-space blade relative to a reference blade image; and
   applying motion correction to the blade image using the motion parameters to generate a motion-corrected blade image; and
   outputting the motion-corrected blade image as the reconstructed blade image.

4. The method of claim 3, wherein the phase correction is computed by subtracting windowed phase data from the blade image from itself in order to remove low-frequency spatially varying components in the blade image.

5. The method of claim 4, wherein the windowed phase data are generated by applying a triangular window to the phase data from the blade image.

6. The method of claim 3, wherein the motion parameters are estimated using a centrally overlapping region of the blade image and the reference blade image.

7. The method of claim 3, wherein the motion parameters are estimated for each time point within the hybrid space for the given blade.

8. The method of claim 3, wherein applying motion correction to the blade image comprises at least one of rotation correction or translation correction.

9. The method of claim 3, further comprising computing a correlation weighting between the reconstructed blade image and the motion-corrected blade image, wherein combining the reconstructed blade images comprises weighting each blade image by its corresponding correlation weighting.

10. The method of claim 2, further comprising accessing calibration data and wherein reconstructing each blade image comprises:
    generating rotated calibration data for the given k-space blade by applying a rotation to the calibration data to align the calibration data with the given k-space blade; and
    reconstructing the blade image using the rotated calibration data and the hybrid space data in the given k-space blade.

11. The method of claim 10, wherein reconstructing each blade image comprises:
    estimating motion parameters based on the hybrid space data in the given k-space blade relative to a reference blade image; and
    generating updated calibration data by further rotating the rotated calibration data based on the motion parameters; and
    wherein the blade image is reconstructed using the updated calibration data and the hybrid space data in the given k-space blade.

12. The method of claim 2, wherein the reconstructed blade images are combined using a gridding process.

13. The method of claim 12, wherein the gridding process implements a Kaiser-Bessel kernel.

14. The method of claim 2, wherein the acquired data undersample the hybrid space and reconstructing each blade image comprises synthesizing additional data in the hybrid space for the given k-space blade using a reconstruction kernel that spans the phase-encoding k-space dimension and the temporal dimension, wherein the blade image is reconstructed from the hybrid space data in the given k-space blade and the additional data.

15. The method of claim 14, wherein the reconstruction kernel is a tilted reconstruction kernel that is oriented at an angle with respect to the phase-encoding k-space dimension in the hybrid space.

16. The method of claim 1, wherein the zig-zag trajectory comprises a plurality of temporally adjacent linear sections each comprising a plurality of temporally adjacent data samples that are spaced apart along the phase-encoding k-space dimension by a phase encoding spacing and are spaced apart along the temporal dimension by a temporal spacing.

17. The method of claim 16, wherein the temporal spacing is selected to minimize $B_0$-inhomogeneity induced phase and $T_2^*$ decay.

18. A method for producing an image with a magnetic resonance imaging (MRI) system, the steps comprising:
    a) acquiring data with an MRI system by sampling k-space in a plurality of k-space blades, wherein k-space is sampled within each k-space blade along a plurality of interleaved phase encoding lines such that temporally adjacent phase encoding lines are separated in time by a first temporal spacing and phase encoding lines that are adjacent in k-space are separated in time by a second temporal spacing that is greater than the first temporal spacing, and
    b) reconstructing an image from the acquired data by reconstructing a blade image for each k-space blade and combining the blade images, generating output as the reconstructed image.

* * * * *